United States Patent
Itoh

(10) Patent No.: US 7,172,894 B2
(45) Date of Patent: Feb. 6, 2007

(54) REDUCTASE GENE AND USE OF THE SAME

(75) Inventor: Nobuya Itoh, Toyama (JP)

(73) Assignee: Sumitomo Chemical Company Limited, Osaka (JP)

(*) Notice: Subject to any disclaimer, the term of this patent is extended or adjusted under 35 U.S.C. 154(b) by 0 days.

(21) Appl. No.: 10/782,998

(22) Filed: Feb. 20, 2004

(65) Prior Publication Data

US 2004/0171119 A1 Sep. 2, 2004

(30) Foreign Application Priority Data

Feb. 28, 2003 (JP) ............................. 2003-053568

(51) Int. Cl.
*C12N 9/02* (2006.01)
*C07H 21/04* (2006.01)

(52) U.S. Cl. .................. 435/252.3; 435/148; 435/155; 435/156; 435/161; 435/170; 435/189; 435/320.1; 435/325; 435/440; 435/252.3; 536/23.2

(58) Field of Classification Search ................ 435/189, 435/148, 155, 156, 161, 170, 320.1, 325; 536/23.2

See application file for complete search history.

(56) References Cited

U.S. PATENT DOCUMENTS 5,385,833 A 1/1995 Bradshaw et al.

OTHER PUBLICATIONS

Matsuda et al, Two classes of opposite stereochemistry in an organism: One for fluorinated and another for nonfluorinated substrates. J. Org. Chem 2000, 65, 157-163.*
Umeyama, T., et al., "Streptomyces coelicor orf1, orf2, orf3, orf4, orf5 genes complete cds.", The University of Tokyo, Department of Biotechnology, Division of Agriculture and Life Sciences (Aug. 1999).
Umeyama, T., et al., "Orf1, orf2, orf3, orf4, orf5 genes", The University of Tokyo, Department of Biotechnology, Division of Agriculture and Life Sciences (May 2000).
Itoh, N., et al., "Cloning and expression in *Escherichia coli* of the gene encoding phenyl trifuloromethyl ketone reductase from *Leifsonia sp. S749*", *Journal of Bioscience and Bioengineering*, vol. 96, No. 1, p. A14 (Jul. 2003).
Inoue, K., et al., "Production of chiral alcohols by enantioselective reduction with phenyl trifluoromethyl ketone reductase (PTKR) from Leifsonia sp. S749", 7th Japanese Symposium on the Chemistry of Biocatalysts (Dec. 2003).
Masaru, W., et al., "Purification and Characterization of Monovalent Cation-Activated Levodione Reductase from *Corynebacterium aquaticum* M-13", Applied and Environmental Microbiology, pp. 4399-4403 (Oct. 1999).
Yoshisumi, A., et al., "Cloning, Sequence Analysis, and Expression in *Escherichia coli* of the Gene Enconding Monovalent Cation-Activated Levodione Reductase from *Corynebacterium aquaticum* M-13", *Biosci. Biotechnol. Biochem.*, vol. 65, No. 4, pp. 830-836 (2001).

Bradshaw, C., et al., "*Lactobacillus kefir* Alcohol Dehydrogenase: A Useful Catalyst for Synthesis", *J. Org. Chem.*, vol. 57, pp. 1532-1536 (1992).
Matsuda, T., et al., "Two classes of enzymes of opposite stereochemistry in an organism: One for fluorinated and another for nonfluorinated substrates," *J. Org. Chem.*, vol. 65, pp. 157-163 (2000).
Suzuki, K., et al., "*Leifsonia* gen. nov., a genus for 2,4-diaminobutyric acid-containing actinomycetes to accommodate '*Corynebacterium aquaticum*' Leifson 1962 and *Clavibacter xyli* subsp. *cynodontis*", *J. Gen. Appl. Microbiol.*, vol. 45, pp. 253-262 (1999).
Hummel, W., "New Alcohol Dehydrogenases for the Synthesis of Chiral Compounds", *Advances in Biochemical Engineering/Biotechnology*, vol. 58, pp. 145-184 (1997).
Nakamura, K., et al., "Recent developments in asymmetric reduction of ketones with biocatalysts", *Tetrahedron: Asymmetry Report No. 60*, vol. 14, pp. 2659-2681 (2003).
Bradshaw, et al., "A *Pseudomonas* sp. Alcohol Dehydrogenase with Broad Substrate Specificity and Unusual Stereospecificity for Organic Synthesis", *J. Org. Chem.*, 57, pp. 1526-1532 (1992).
Bradshaw, et al., "*Lactobacillus kefir* Alcohol Dehydrogenase: A Useful Catalyst for Synthesis", *J. Org. Chem.*, 57, pp. 1532-1536 (1992).
Wong, et al., "Enzymatic vs. Fermentative Synthesis: Thermostable Glucose Dehydrogenase Catalyzed Regeneration of NAD(P)H for use in Enzymatic Synthesis", *J. Am. Chem. Soc.*, 107, pp. 4028-4031 (1985).
Yamazaki, et al., "Stereoselectivity in the Microbial Reduction of (Trifluoroacetyl)ferrocene and 2-Fluoroacetophenones", *Tetrahedron: Asymmetry*, vol. 4, No. 6, pp. 1287-1294 (1993).
Bernardi, et al., "Production of (R)-1-(1,3-Dithian-2-yl)propan-2-ol by Microbial Reduction", *J. Chem. Soc. Perkin Trans.*, 1, pp. 1607-1608 (1987).
Nakamura, et al., "Different Stereochemistry for the Reduction of Trifluoromethyl Ketones and MEthyl Ketones Catalyzed by Alcohol Dehydrogenase from *Geotrichum*", *Tetrahedron Letters*, vol. 37, No. 32, pp. 5727-5730 (1996).

* cited by examiner

*Primary Examiner*—Rebecca E. Prouty
*Assistant Examiner*—Kagnew Gebreyesus
(74) *Attorney, Agent, or Firm*—Akin Gump Strauss Hauer & Feld, LLP

(57) ABSTRACT

A gene containing a DNA having the nucleotide sequence encoding any one of the amino acid sequences of the following (a) to (e):

(a) an amino acid sequence set out in SEQ ID NO: 1;
(b) an amino acid sequence having the sequence homology of 80% or more with (a);
(c) an amino acid sequence having the sequence homology of 90% or more with (a);
(d) an amino acid sequence encoded by a DNA having the nucleotide sequence set out in SEQ ID NO: 2;
(e) an amino acid sequence encoded by a DNA having the nucleotide sequence having the sequence homology of 80% or more with (d).

8 Claims, No Drawings

SEQUENCE LISTING

```
<160> NUMBER OF SEQ ID NOS: 14

<210> SEQ ID NO 1
<211> LENGTH: 250
<212> TYPE: PRT
<213> ORGANISM: Leifsonia sp.

<400> SEQUENCE: 1

Met Ala Gln Tyr Asp Val Ala Asp Arg Ser Ala Ile Val Thr Gly Gly
1               5                   10                  15

Gly Ser Gly Ile Gly Arg Ala Val Ala Leu Thr Leu Ala Ala Ser Gly
            20                  25                  30

Ala Ala Val Leu Val Thr Asp Leu Lys Glu Glu His Ala Gln Ala Val
        35                  40                  45

Val Ala Glu Ile Glu Ala Ala Gly Gly Lys Ala Ala Ala Leu Ala Gly
    50                  55                  60

Asp Val Thr Asp Pro Ala Phe Gly Glu Ala Ser Val Ala Gly Ala Asn
65                  70                  75                  80

Ala Leu Ala Pro Leu Lys Ile Ala Val Asn Asn Ala Gly Ile Gly Gly
                85                  90                  95

Glu Ala Ala Thr Val Gly Asp Tyr Ser Leu Asp Ser Trp Arg Thr Val
            100                 105                 110

Ile Glu Val Asn Leu Asn Ala Val Phe Tyr Gly Met Gln Pro Gln Leu
        115                 120                 125
```

```
Lys Ala Met Ala Ala Asn Gly Gly Ala Ile Val Asn Met Ala Ser
            130                 135                 140

Ile Leu Gly Ser Val Gly Phe Ala Asn Ser Ser Gly Tyr Val Thr Ala
145                 150                 155                 160

Lys His Ala Leu Leu Gly Leu Thr Gln Asn Ala Ala Leu Glu Tyr Ala
                165                 170                 175

Ala Asp Lys Val Arg Val Ala Val Gly Pro Gly Phe Ile Arg Thr
            180                 185                 190

Arg Ser Trp Arg Gln Leu Phe Arg Arg Ala Gly Val Leu Gln Gly
        195                 200                 205

Lys His Ala Leu Gly Arg Leu Gly Glu Pro Glu Val Ala Ser Leu
    210                 215                 220

Val Ala Phe Leu Ala Ser Asp Ala Ala Ser Phe Ile Thr Gly Ser Tyr
225                 230                 235                 240

His Leu Val Asp Gly Gly Tyr Thr Ala Gln
                245                 250

<210> SEQ ID NO 2
<211> LENGTH: 753
<212> TYPE: DNA
<213> ORGANISM: Leifsonia sp.
<220> FEATURE:
<221> NAME/KEY: CDS
<222> LOCATION: (1)..(753)

<400> SEQUENCE: 2 atg gct cag tac gac gtc gcc gac cgg tcc gcg atc gtg acc gga ggc        48
Met Ala Gln Tyr Asp Val Ala Asp Arg Ser Ala Ile Val Thr Gly Gly
1               5                   10                  15 ggc tcg ggc atc ggg cgc gcc gtg gcg ctc act ctc gcg gcg agc ggc        96
Gly Ser Gly Ile Gly Arg Ala Val Ala Leu Thr Leu Ala Ala Ser Gly
                20                  25                  30 gca gcc gtc ctc gtc acc gac ctg aaa gag gag cac gcg cag gcc gtc       144
Ala Ala Val Leu Val Thr Asp Leu Lys Glu Glu His Ala Gln Ala Val
            35                  40                  45 gtg gcc gag atc gag gcc gcg ggc ggt aag gcc gcc gcg ctc gcg ggc       192
Val Ala Glu Ile Glu Ala Ala Gly Gly Lys Ala Ala Ala Leu Ala Gly
        50                  55                  60 gac gtg acc gac ccc gcg ttc ggc gag gcg agc gtc gcc ggg gcg aac       240
Asp Val Thr Asp Pro Ala Phe Gly Glu Ala Ser Val Ala Gly Ala Asn
65                  70                  75                  80 gct ctc gcg ccc ctc aag atc gcg gtc aac aac gcg ggc atc ggc ggc       288
Ala Leu Ala Pro Leu Lys Ile Ala Val Asn Asn Ala Gly Ile Gly Gly
                85                  90                  95 gag gcc gcc acg gtc ggc gac tac tcg ctc gac agc tgg cgc acg gtg       336
Glu Ala Ala Thr Val Gly Asp Tyr Ser Leu Asp Ser Trp Arg Thr Val
                100                 105                 110 atc gag gtc aac ctc aac gcc gtg ttc tac ggg atg cag ccg cag ctg       384
Ile Glu Val Asn Leu Asn Ala Val Phe Tyr Gly Met Gln Pro Gln Leu
            115                 120                 125 aag gcc atg gcc gcc aac ggc ggc ggt gcg atc gtc aac atg gcg tcc       432
Lys Ala Met Ala Ala Asn Gly Gly Gly Ala Ile Val Asn Met Ala Ser
        130                 135                 140 atc ctc gga agc gtc ggc ttc gcc aac tcg tcg ggc tac gtc acg gcc       480
Ile Leu Gly Ser Val Gly Phe Ala Asn Ser Ser Gly Tyr Val Thr Ala
145                 150                 155                 160 aag cac gcg ctg ctc ggt ctc acc cag aac gcc gcg ctc gag tac gcc       528
Lys His Ala Leu Leu Gly Leu Thr Gln Asn Ala Ala Leu Glu Tyr Ala
                165                 170                 175
```

```
gcc gac aag gtg cgc gtc gtc gcg gtc ggc ccc ggc ttc atc cgc acc        576
Ala Asp Lys Val Arg Val Val Ala Val Gly Pro Gly Phe Ile Arg Thr
            180                 185                 190 cgc tcg tgg agg caa ctt ttc cgc cga cgc gct ggc gtt ctt caa ggg        624
Arg Ser Trp Arg Gln Leu Phe Arg Arg Arg Ala Gly Val Leu Gln Gly
        195                 200                 205 aag cac gcc ctc ggc cgc ctg ggc gag ccg gaa gag gtc gcc tcg ctg        672
Lys His Ala Leu Gly Arg Leu Gly Glu Pro Glu Glu Val Ala Ser Leu
    210                 215                 220 gtc gcg ttc ctc gcc tcc gac gcc gcg agc ttc atc acc ggc agc tac        720
Val Ala Phe Leu Ala Ser Asp Ala Ala Ser Phe Ile Thr Gly Ser Tyr
225                 230                 235                 240 cac ctg gtg gac ggc ggc tac acc gcc cag tga                            753
His Leu Val Asp Gly Gly Tyr Thr Ala Gln
                245                 250

<210> SEQ ID NO 3
<211> LENGTH: 20
<212> TYPE: DNA
<213> ORGANISM: Artificial sequence
<220> FEATURE:
<223> OTHER INFORMATION: Designed oligonucleotide primer for PCR

<400> SEQUENCE: 3
atggctcagt acgacgtcgc                                                   20

<210> SEQ ID NO 4
<211> LENGTH: 20
<212> TYPE: DNA
<213> ORGANISM: Artificial Sequence
<220> FEATURE:
<223> OTHER INFORMATION: Designed oligonucleotide primer for PCR

<400> SEQUENCE: 4
tcactgggcg gtgtagccgc                                                   20

<210> SEQ ID NO 5
<211> LENGTH: 15
<212> TYPE: PRT
<213> ORGANISM: Leifsonia sp.

<400> SEQUENCE: 5

Ala Gln Tyr Asp Val Ala Asp Arg Ser Ala Ile Val Thr Gly Gly
1               5                   10                  15

<210> SEQ ID NO 6
<211> LENGTH: 12
<212> TYPE: PRT
<213> ORGANISM: Leifsonia sp.

<400> SEQUENCE: 6

Ile Ala Val Asn Asn Ala Gly Ile Gly Gly Glu Ala
1               5                   10

<210> SEQ ID NO 7
<211> LENGTH: 20
<212> TYPE: DNA
<213> ORGANISM: Artificial Sequence
<220> FEATURE:
<223> OTHER INFORMATION: Designed oligonucleotide primer for PCR
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
```

```
<222> LOCATION: (15)..(15)
<223> OTHER INFORMATION: n is a, c, g, or t

<400> SEQUENCE: 7
cartaygayg tngcngahmg                                                  20

<210> SEQ ID NO 8
<211> LENGTH: 20
<212> TYPE: DNA
<213> ORGANISM: Artificial sequence
<220> FEATURE:
<223> OTHER INFORMATION: Designed oligonucleotide primer for PCR
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 8
ccdatnccng crttrttnac                                                  20

<210> SEQ ID NO 9
<211> LENGTH: 304
<212> TYPE: DNA
<213> ORGANISM: Leifsonia sp.

<400> SEQUENCE: 9
gaattcgatt cagtatgatg tggctgatcg gtccgcgatc gtgaccggag gcggctcagg      60
catcgggcgc gccgtggcgc tcactctcgc ggcgagcggc gcagccgtcc tcgtcaccga    120
cctgaacgag gagcacgcgc aggccgtcgt ggccgagatc gaggccgcgg gcggtaaggc    180
cgccgcgctc gcgggcgacg tgaccgaccc cgcgttcggc gaggcgagcg tcgccggggc    240
gaacgctctc gcgcccctca agatcgcggt caataacgca ggcatcggaa tcactagtga    300
attc                                                                 304

<210> SEQ ID NO 10
<211> LENGTH: 304
<212> TYPE: DNA
<213> ORGANISM: Leifsonia sp.

<400> SEQUENCE: 10
gaattcgatt cagtatgatg tggctgatcg gtccgcgatc gtgaccggag gcggctcagg      60
catcgggcgc gccgtggcgc tcactctcgc ggcgagcggc gcagccgtcc tcgtcaccga    120
cctgaacgag gagcacgcgc aggccgtcgt ggccgagatc gaggccgcgg gcggtaaggc    180
cgccgcgctc gcgggcgacg tgaccgaccc cgcgttcggc gaggcgagcg tcgccggggc    240
gaacgctctc gcgcccctca agatcgcggt caataacgca ggcatcggaa tcactagtga    300
attc                                                                 304

<210> SEQ ID NO 11
<211> LENGTH: 26
<212> TYPE: DNA
<213> ORGANISM: Artificial sequence
<220> FEATURE:
<223> OTHER INFORMATION: Designed oligonucleotide primer for PCR
```

-continued

```
<400> SEQUENCE: 11
ggagatttcc atggctcagt acgacg                                              26

<210> SEQ ID NO 12
<211> LENGTH: 20
<212> TYPE: DNA
<213> ORGANISM: Artificial Sequence
<220> FEATURE:
<223> OTHER INFORMATION: Designed oligonucleotide primer for PCR

<400> SEQUENCE: 12
gggctgcagc ccggtcactg                                                     20

<210> SEQ ID NO 13
<211> LENGTH: 29
<212> TYPE: DNA
<213> ORGANISM: Artificial Sequence
<220> FEATURE:
<223> OTHER INFORMATION: Designed oligonucleotide primer for PCR

<400> SEQUENCE: 13
gctgcagcga tcatcatagc aggagtcat                                           29

<210> SEQ ID NO 14
<211> LENGTH: 31
<212> TYPE: DNA
<213> ORGANISM: Artificial Sequence
<220> FEATURE:
<223> OTHER INFORMATION: Designed oligonucleotide primer for PCR

<400> SEQUENCE: 14
acaagcttgt gaattcaaca ccagtcagct c                                        31
```

REDUCTASE GENE AND USE OF THE SAME

BACKGROUND OF THE INVENTION

1. Field of the Invention

The present invention relates to a gene encoding a reductase, the enzyme, and the use of the same.

2. Description of the Related Art

Alcohols are useful compounds as intermediates of various kinds of application-imparted compounds, and the like. Many methods for producing an alcohol have been hitherto known. In particular, optically active alcohols are useful compounds as intermediates of medicines and agricultural chemicals, and thus, a variety of methods for producing an alcohol have been proposed hitherto.

Examples of the methods for producing an optically active alcohol as described above include methods of the extraction from a natural product, methods of the optical resolution of a racemic compound, methods for using a asymmetric catalyst, and the like. However the methods for producing an optically active alcohol were generally complicated. Hence, development of a simple production method which is able to apply the production of an optically active alcohol has been desired.

SUMMARY OF THE INVENTION

The present inventors studied for a method for producing an optically active alcohol with few problems as described above, and consequently found a gene encoding a kind of an amino acid sequence, and an optically active alcohol can be easily produced with a protein having said amino acid sequence.

That is, the present invention provides the following [1] to [22].

[1] A gene comprising a DNA having the nucleotide sequence encoding any one of the amino acid sequences of the following (a) to (h):

(a) an amino acid sequence set out in SEQ ID NO: 1;

(b) an amino acid sequence having the sequence homology of 80% or more with the amino acid sequence set out in SEQ ID NO: 1, and the amino acid sequence is an amino acid sequence of a protein having at least an ability to reduce 2,2,2-trifluoroacetophenone to 2,2,2-trifluoro-1-phenylethanol;

(c) an amino acid sequence having the sequence homology of 90% or more with the amino acid sequence set out in SEQ ID NO: 1, and the amino acid sequence is an amino acid sequence of a protein having at least an ability to reduce 2,2,2-trifluoroacetophenone to 2,2,2-trifluoro-1-phenylethanol;

(d) an amino acid sequence encoded by a DNA having the nucleotide sequence set out in SEQ ID NO: 2;

(e) an amino acid sequence encoded by a DNA having the nucleotide sequence having the sequence homology of 80% or more with a DNA having the nucleotide sequence set out in SEQ ID NO: 2, and the amino acid sequence is an amino acid sequence of a protein having at least an ability to reduce 2,2,2-trifluoroacetophenone to 2,2,2-trifluoro-1-phenylethanol;

(f) an amino acid sequence encoded by a DNA that hybridizes under the stringent condition with a DNA having a nucleotide sequence which is complementary to the nucleotide sequence set out in SEQ ID NO: 2, and the amino acid sequence is an amino acid sequence of a protein having at least an ability to reduce 2,2,2-trifluoroacetophenone to 2,2,2-trifluoro-1-phenylethanol;

(g) an amino acid sequence of a protein obtained from a microorganism belonging to genus *Leifsonia*, and the amino acid sequence is an amino acid sequence of a protein having at least an ability to reduce 2,2,2-trifluoroacetophenone to 2,2,2-trifluoro-1-phenylethanol; and (h) an amino acid sequence of a protein obtained from *Leifsonia* sp. S-749, and the amino acid sequence is an amino acid sequence of a protein having at least an ability to reduce 2,2,2-trifluoroacetophenone to 2,2,2-trifluoro-1-phenylethanol.

[2] The gene according to [1] further comprising a linked promoter.

[3] A recombinant vector comprising the gene according to [1] or [2].

[4] A transformant obtained by introducing the gene according to [2] or the recombinant vector according to [3] into a host cell.

[5] The transformant according to [4], wherein the host cell is a microorganism.

[6] The transformant according to [4], wherein the host cell is *E. coli*.

[7] A transformant having the gene according to [1].

[8] A method for producing a transformant, wherein the method comprises the step of introducing the recombinant vector according to [3] into a host cell.

[9] A protein having the amino acid sequence according to [1].

[10] A method for producing an alcohol, wherein the method comprises the step of contacting a ketone compound or an aldehyde compound with the protein according to [9], a microorganism that produces the protein according to [9], the transformant according to any one of [4] to [7], or a processed product thereof.

[11] The recombinant vector according to [3] further comprising a gene having a DNA having a nucleotide sequence encoding an amino acid sequence of a protein having an ability to convert oxidized β-nicotinamide adenine dinucleotide into the reduced form thereof.

[12] The recombinant vector according to [11], wherein the protein having an ability to convert oxidized β-nicotinamide adenine dinucleotide into the reduced form thereof is glucose dehydrogenase.

[13] A transformant obtained by introducing the recombinant vector according to [11] or [12] into a host cell.

[14] The transformant according to [13], wherein the host cell is a microorganism.

[15] The transformant according to [13], wherein the host cell is *E. coli*.

[16] A transformant having the gene according to [1], and a gene comprising a DNA having a nucleotide sequence encoding an amino acid sequence of a protein having an ability to convert oxidized β-nicotinamide adenine dinucleotide into the reduced form thereof.

[17] The method according to [10], wherein a protein having an ability to convert oxidized β-nicotinamide adenine dinucleotide into the reduced form thereof is allowed to coexist in the reaction system.

[18] The method according to [17], wherein the protein having an ability to convert oxidized β-nicotinamide adenine dinucleotide into the reduced form thereof is glucose dehydrogenase.

[19] A method for producing an alcohol, wherein the method comprises the step of contacting a ketone compound or an aldehyde compound with the transformant according to any one of [13] to [16], or a processed product thereof.

[20] *Leifsonia* sp. S-749 (Accession No. of International Depositary Authority: FERM BP-8291).

[21] Use of a microorganism belonging to genus *Leifsonia* as a catalyst for producing an alcohol from a ketone compound or an aldehyde compound.

[22] Use according to [21], wherein the microorganism belonging to genus *Leifsonia* is *Leifsonia* sp. S-749 (Accession No. of International Depositary Authority: FERM BP-8291).

DETAILED DESCRIPTION OF THE INVENTION

First, the gene of the present invention is illustrated.

A gene of the present invention comprises a DNA having the nucleotide sequence encoding the following amino acid sequence:

(a) an amino acid sequence set out in SEQ ID NO: 1;

(b) an amino acid sequence having the sequence homology of 80% or more with the amino acid sequence set out in SEQ ID NO: 1, and the amino acid sequence is an amino acid sequence of a protein having at least an ability to reduce 2,2,2-trifluoroacetophenone to 2,2,2-trifluoro-1-phenylethanol;

(c) an amino acid sequence having the sequence homology of 90% or more with the amino acid sequence set out in SEQ ID NO: 1, and the amino acid sequence is an amino acid sequence of a protein having at least an ability to reduce 2,2,2-trifluoroacetophenone to 2,2,2-trifluoro-1-phenylethanol;

(d) an amino acid sequence encoded by a DNA having the nucleotide sequence set out in SEQ ID NO: 2;

(e) an amino acid sequence encoded by a DNA having the nucleotide sequence having the sequence homology of 80% or more with a DNA having the nucleotide sequence set out in SEQ ID NO: 2, and the amino acid sequence is an amino acid sequence of a protein having at least an ability to reduce 2,2,2-trifluoroacetophenone to 2,2,2-trifluoro-1-phenylethanol;

(f) an amino acid sequence encoded by a DNA that hybridizes under the stringent condition with a DNA having a nucleotide sequence which is complementary to the nucleotide sequence set out in SEQ ID NO: 2, and the amino acid sequence is an amino acid sequence of a protein having at least an ability to reduce 2,2,2-trifluoroacetophenone to 2,2,2-trifluoro-1-phenylethanol;

(g) an amino acid sequence of a protein that can be obtained from a microorganism belonging to genus *Leifsonia*, and the amino acid sequence is an amino acid sequence of a protein having at least an ability to reduce 2,2,2-trifluoroacetophenone to 2,2,2-trifluoro-1-phenylethanol;

(h) an amino acid sequence of a protein obtained from *Leifsonia* sp. S-749, and the amino acid sequence is an amino acid sequence of a protein having at least an ability to reduce 2,2,2-trifluoroacetophenone to 2,2,2-trifluoro-1-phenylethanol.

The DNA having a nucleotide sequence encoding the amino acid sequence set out in SEQ ID NO: 1 is a DNA having a nucleotide sequence encoding an amino acid sequence of a protein having an ability of the asymmetric reduction of 2,2,2-trifluoroacetophenone to produce (S)-2,2,2-trifluoro-1-phenylethanol predominantly. Optically active alcohol can be easily produced by contacting a ketone compound with a transformant obtained by introducing said DNA into a host cell, or a processed product thereof.

The gene of the present invention may be a natural gene, or may be a gene generated by introducing a mutation (site-directed mutagenesis, mutagenesis or the like) into a natural gene. When screening a natural gene, the target may be any microorganism having at least an ability to reduce 2,2,2-trifluoroacetophenone to 2,2,2-trifluoro-1-phenylethanol. Examples of the target may include microorganisms belonging to genus *Leifsonia*.

These microorganisms may be isolated from the natural environment, or may be purchased from a strain preserving organization or the like.

When isolating from the natural environment, soil is first collected from the field. After suspending the collected soil in sterile water, the suspension is applied, for example, on a solid medium for isolation of a microorganism such as a PY medium (after dissolving 5 g/L of Bacto Peptone, and 5 g/L of Yeast Extract in water, pH is adjusted to 7.0) or the like. The solid medium is cultured at 25° C., and the independent colony grown after a few days is collected, and transplanted on a fresh solid medium such as a PY medium for isolation of a microorganism, and further cultured at 25° C. A microorganism belonging to genus *Leifsonia* may be selected by identifying said grown microorganism whether it is a microorganism belonging to genus *Leifsonia* or not, according to the process described in SNEATH, (P.H.A.). MAIR, (N.S.) SHARPE, (M.E.) and HOLT, (J.G.): Bergey's manual of Systematic Bacteriology. Vol. 2. 1984, Williams and Wilkins, Baltimore and the like.

Next, a microorganism belonging to genus *Leifsonia* used in the present invention may be selected from thus selected microorganism belonging to genus *Leifsonia* by determining the presence of an ability of the microorganism to reduce 2,2,2-trifluoroacetophenone to 2,2,2-trifluoro-1-phenylethanol, according to, for example, the method as described in Examples below.

*Leifsonia* sp. S-749 strain was deposited with International Patent Organism Depositary, National Institute of Advanced Industrial Science and Technology, and assigned Accession No. of FERM BP-8291 (Date of Original Deposit: Feb. 12, 2003). Mycological characters are as follows.

1. Morphology of Colony (30° C., 48 hours)
    (1) Shape of cells: bacillus, 0.6×1.0 to 2.0 μm
    (2) Gram stain: positive
    (3) Presence of spores: absent
    (4) Presence of motility: present
2. Morphology of Colony on Nutrient Agar
    Color of colony: yellow
    Shape of colony: circular
    Margin of colony: smooth at entire margin
    Prominence of colony: low convex
3. Physiological Characters
    (1) Catalase: positive
    (2) Oxidase: negative
    (3) OF test: positive/negative
4. Nucleotide sequence of DNA coding for 16S ribosomal RNA A nucleotide sequence of 16S ribosomal DNA of about 500 bp was amplified from *Leifsonia* sp. S-749 strain by PCR to analyze the nucleotide sequence. Using thus obtained nucleotide sequence of 16S ribosomal DNA, BLAST homology search was conducted. Consequently, the highest homology was indicated to 16S ribosomal DNA of *Leifsonia aquatica* type strain with the homology of 99.6%. Further, among top 5 strains searched, *Leifsonia* occupied four strains, with the homology of 98% or more.

From the mycological characters described above, the present microorganism was identified as *Leifsonia* sp.

The gene of the preset invention comprises a nucleotide sequence encoding an amino acid sequence of a protein having an ability to catalyze a reductive reaction to reduce 2,2,2-trifluoroacetophenone to 2,2,2-trifluoro-1-phenylethanol.

In the gene of the present invention, the amino acid sequence set out in SEQ ID NO: 1 according to one letter notation is:

MAQYDVADRSAIVTGGGSGIGRAVALTLAASGAAVLVTDLKEEHAQAVVAEIEAAGGKAAALA

GDVTDPAFGEASVAGANALAPLKIAVNNAGIGGEAATVGDYSLDSWRTVIEVNLNAVFYGMQ

PQLKAMAANGGGAIVNMASILGSVGFANSSGYVTAKHALLGLTQNAALEYAADKVRVVAVGP

GFIRTRSWRQLFRRRAGVLQGKHALGRLGEPEEVASLVAFLASDAASFITGSYHLVDGGYTA

Q

The gene of the present invention involves "genes including deletion, addition or substitution of one or more amino acids", "genes having the sequence homology of 80% or more" as in above-mentioned (b) and (e) and the like, which may include, for example, processing that is effected to the protein having the amino acid sequence set out in SEQ ID NO: 1 in a cell; mutations naturally occurring due to species difference, individual difference, difference between tissues of the organism from which the protein originates; artificial mutation; and the like.

As a procedure for artificially achieving "deletion, addition or substitution of one or more amino acids" (hereinafter, may be also referred to as "modification of amino acid") described above, a procedure which comprises subjecting a DNA encoding the amino acid sequence set out in SEQ ID NO: 1 to the conventional site-directed mutagenesis followed by expression of the DNA by means of a routine method may be exemplified. Examples of the site-directed mutagenesis include a method in which amber mutation is utilized (gapped-duplex method, Nucleic Acids Res. 12, 9441–9456 (1984)), a method based on the PCR with the use of a primer for introducing a mutation, and the like.

The number of amino acids to be modified in the above procedure is at least one residue, more specifically one or several, or more residue(s). This number of modification may be any number within the scope not to impair the ability to reduce 2,2,2-trifluoroacetophenone to 2,2,2-trifluoro-1-phenylethanol.

Furthermore, it is preferred that the modification is substitution of the amino acid, in particular, among the deletion, addition and substitution as described above. The substitution is more preferably any substitution for an amino acid having similar properties such as hydrophobicity, charge, pK and conformational features. Examples of such a substitution include substitutions among residues within the following respective groups: (1) glycine, alanine; (2) valine, isoleucine, leucine; (3) aspartic acid, glutamic acid, asparagine, glutamine; (4) serine, threonine; (5) lysine, arginine; (6) phenylalanine, tyrosine.

In the present invention, the term "sequence homology" refers to the identity and homology between sequences of two DNAs or two proteins. The aforementioned "sequence homology" is determined by comparing two sequences aligned in the optimum condition over the sequences to be compared. The DNAs or proteins to be compared herein may have an addition or deletion (for example, gap and the like) in the optimum alignment of the two sequences. Such a sequence homology can be calculated by creating an alignment with the use of, for example, Vector NTI, while utilizing ClustalW algorithm (Nucleic Acid Res., 22(22): 4673–4680 (1994). A sequence homology is measured by using sequence analysis software, more specifically, Vector NTI, GENETYX or analysis tools provided by public databases. The public databases are commonly available, for example, in the URL address of http://www.ddbj.nig.ac.jp.

The sequence homology in the present invention may be preferably 80% or more, more preferably 90% or more, and further preferably 95% or more.

In connection with "hybridize under the stringent condition" as described in the aforementioned (f), the hybridization used herein can be carried out in accordance with a common method such as a method described in Molecular Cloning 2nd edition, published by Cold Spring Harbor Laboratory press, Sambrook J., Frisch E. F. Maniatis T., or the like, and more specifically, Southern hybridization method or the like.

Moreover, examples of the "stringent condition" include (1) a condition of allowing DNA-DNA hybridization between a DNA having the nucleotide sequence set out in SEQ ID NO: 2 and a DNA having a nucleotide sequence that is complementary thereto by the hybridization in a solution containing 50% formamide under a high ion concentration (for example, 6×SSC (a solution containing 1.5 M NaCl and 0.15 M trisodium citrate solution is defined as 10×SSC)) at 45° C., and then washing under a low ion concentration (for example, 2×SSC) at 50° C. (Molecular Biology, John Wiley & Sons, N.Y. (1989), 6.3.1–6.3.6), (2) a condition of allowing DNA-DNA hybridization between a DNA having the nucleotide sequence set out in SEQ ID NO: 2 and a DNA having a nucleotide sequence that is complementary thereto by the hybridization in a solution under a high ion concentration (for example, 6×SSC) at 65° C., and then washing under a low ion concentration (for example, 0.1×SSC) at 65° C. ("Cloning and Sequence" edited by Masahiro Sugiura under the editorship of Itaru Watanabe, published by Nosonbunkasha, 1989), and the like. The salt concentration in the washing step, for example, when the temperature is set to be 50° C., may be selected from between the condition of 2×SSC at 50° C. (low stringency condition) and the condition of 0.2×SSC at 50° C. (high stringency condition). The temperature in the washing step may be selected from, for example, between the room temperature (low stringency condition) and the temperature of 65° C. (high stringency condition). Also, both the salt concentration and the temperature may be changed. DNAs capable of keeping the aforementioned hybrid even after such a washing step are referred to DNAs which hybridize under the stringent condition.

A DNA having a gene of the present invention may be prepared, for example, as described below.

A DNA having a gene of the present invention may be obtained by: preparing a DNA library from a microorganism or the like belonging to genus *Leifsonia* in accordance with a commonly employed genetic engineering technique (for example, a method described in "New Cell Engineering Laboratory Protocol" (edited by Department of Oncology, Institute of Medical Science, Univ. of Tokyo, Syujunsya, 1993)); amplifying a DNA having a nucleotide sequence encoding the amino acid sequence set out in SEQ ID NO: 1, a DNA having a nucleotide sequence encoding an amino acid sequence including deletion, substitution or addition of one or more amino acid(s) in the amino acid sequence set out in SEQ ID NO: 1, and/or a DNA having the nucleotide sequence set out in SEQ ID NO: 2 or the like, through conducting PCR with the prepared DNA library as a template while using an appropriate primer.

In this procedure, when the PCR is conducted with the aforementioned DNA library as a template while using an oligonucleotide having the nucleotide sequence set out in SEQ ID NO: 3 and an oligonucleotide having the nucleotide sequence set out in SEQ ID NO: 4 as primers, a DNA having the nucleotide sequence set out in SEQ ID NO: 2 is amplified, whereby a DNA having a gene of the present invention is prepared.

The condition for the above PCR may be, for example, such a condition that comprises heating a reaction mixture including the mixture of each 20 µM of four kinds of dNTPs, each 15 pmol of two kinds of oligonucleotide primers, 1.3 U of Taqpolymerase and a DNA library which serves as a template at 94° C. for 5 min., repeating a cycle of 94° C. for 5 min., 55° C. for 0.5 min. and 72° C. for 0.5 min. for 30 times, and holding the mixture at 72° C. for 10 min.

At the 5' ends of the primers for use in the above PCR may be added a sequence recognized by a restriction enzyme.

Also, a DNA having a gene of the present invention may be prepared by amplifying a DNA having a nucleotide sequence encoding the amino acid sequence set out in SEQ ID NO: 1, a DNA having a nucleotide sequence encoding an amino acid sequence including deletion, substitution or addition of one or more amino acid(s) in the amino acid sequence set out in SEQ ID NO: 1 or the like, through conducting PCR with the aforementioned DNA library as a template while using an oligonucleotide having a partial nucleotide sequence selected from the nucleotide sequence encoding the amino acid sequence set out in SEQ ID NO: 1 or the like (for example, an oligonucleotide having a nucleotide sequence of approximately 14 bases or more at 5' end which encodes the amino acid sequence set out in SEQ ID NO: 1) and an oligonucleotide of approximately 14 bases or more having a nucleotide sequence that is complementary to the nucleotide sequence in the vicinity of the insertion site of the DNA of the vector employed for the construction of the DNA library, as primers.

The DNA amplified in the manner as described above can be cloned into a vector in accordance with a method as described in "Molecular Cloning: A Laboratory Manual 2$^{nd}$ edition" (1989), Cold Spring Harbor Laboratory Press, "Current Protocols in Molecular Biology" (1987), John Wiley & Sons, Inc. ISBN 0-471-50338-X and the like to thereby obtain a recombinant vector of the present invention. Specific examples of the vector which may be used include pUC119 (manufactured by TAKARA SYUZO CO., LTD.), pTV118N (manufactured by TAKARA SYUZO CO., LTD.), pBluescriptII (manufactured by TOYOBO CO., LTD.), pCR2.1-TOPO (manufactured by Invitrogen Corporation), pTrc99A (manufactured by Pharmacia Corporation), pKK223-3 (manufactured by Pharmacia Corporation) and the like.

In addition, a DNA having a gene of the present invention can be also obtained by, for example, allowing hybridization of a DNA library, which was inserted into a vector derived from a microorganism or a phage, with a DNA having a nucleotide sequence of approximately 15 bases or more having a partial nucleotide sequence selected from a nucleotide sequence encoding the amino acid sequence set out in SEQ ID NO: 1 as a probe under the condition as described below, and detecting a DNA that specifically binds with such a probe.

Examples of the process for allowing hybridization of a chromosomal DNA or a DNA library with a probe include colony hybridization and plaque hybridization, which process may be selected depending on the type of the vector used for the production of the library.

When the library used is produced using a plasmid vector, colony hybridization may be preferably utilized. More specifically, a transformant is obtained by introducing the DNA of the library into a host microorganism, and diluting the obtained transformant, and placing the diluted transformant on an agar medium, and culturing until a colony appears.

When the library used is produced using a phage vector, plaque hybridization may be preferably utilized. More specifically, the host microorganism and phage of the library is admixed under the condition in which infection is permitted, and further mixed with a soft agar medium. Thereafter, the mixture is plated on an agar medium, and cultured until a plaque appears.

Next, in either case of hybridization, a membrane is placed on the agar medium cultured as described above, and thus the transformant or the phage is adsorbed and transferred on the membrane. After subjecting this membrane to an alkaline treatment, it is subjected to a neutralization treatment followed by a treatment for fixing the DNA on the membrane. More specifically, for example, in case of plaque hybridization, a nitrocellulose membrane or a nylon membrane (for example, Hybond-N$^+$ (registered trademark, Amersham Corporation)) is placed on the aforementioned agar medium, and left to stand still for about 1 min. to allow the phage particle to adsorb and transfer on the membrane. Next, the membrane is immersed in an alkaline solution (for example, 1.5 M sodium chloride, 0.5 M sodium hydroxide) for about 3 min. to dissolve the phage particle, thereby allowing the phage DNA to elute on the membrane, and the membrane is immersed in a neutralization solution (for example, 1.5 M sodium chloride, 0.5 M Tris-HCl buffer solution, pH 7.5) for about 5 min. Then, after washing the membrane with a washing solution (for example, 0.3 M sodium chloride, 30 mM citric acid, 0.2 M Tris-HCl buffer solution, pH 7.5) for about 5 min., the phage DNA is fixed on the membrane by heating, for example, at about 80° C. for about 90 min.

Using the membrane prepared in such a manner, hybridization is carried out using the aforementioned DNA as a probe. The hybridization can be carried out in accordance with, for example, description of J. Sambrook. E. F. Frisch. T. Maniatis "Molecular Cloning: A Laboratory Manual 2$^{nd}$ edition (1989)", Cold Spring Harbor Laboratory Press, and the like.

The DNA used for the probe may be labelled with a radioisotope, or may be labelled with a fluorescent dye.

As a process for labeling the DNA used for a probe with a radioisotope, for example, aprocess in which PCR is conducted with the DNA used for the probe as a template, through converting dCTP into ($\alpha$-$^{32}$P)dCTP in the PCR reaction mixture by utilizing Random Primer Labeling Kit (manufactured by TAKARA SYUZO CO., LTD.) may be involved.

When the DNA used for the probe is labelled with a fluorescent dye, for example, ECL Direct Nucleic Acid Labeling and Detection System manufactured by Amersham Corporation or the like may be used.

The hybridization can be carried out, for example, as described below.

A prehybridization liquid is provided at a ratio of 50 to 200 μl per 1 cm² of the membrane produced as described above, and the aforementioned membrane is immersed in the prehybridization liquid and incubated at 42 to 65° C. for 1 to 4 hours. The prehybridization liquid used contains 450 to 900 mM sodium chloride, 45 to 90 mM sodium citrate, 0.1 to 1.0% by weight of sodium dodecylsulfate (SDS), non-specific denatured DNA at the concentration of 0 to 200 μg/ml, and may contain albumin, Ficoll, polyvinylpyrrolidone and the like at the concentration of 0 to 0.2% by weight, respectively. The prehybridization liquid preferably contains 900 mM sodium chloride, 90 mM sodium citrate, 1.0% by weight SDS and 100 μg/ml denatured Calf-thymus DNA.

Then, for example, a hybridization liquid mixed with the probe (an amount corresponding to $1.0 \times 10^4$ to $2.0 \times 10^6$ cpm per 1 cm² of the membrane) to obtain a hybridization solution, and the obtained hybridization solution is provided at a ratio of 50 to 200 μl per 1 cm² of the membrane, and the aforementioned membrane is immersed in such a hybridization solution and incubated at 42 to 65° C. for 12 to 20 hours. The hybridization liquid contains 450 to 900 mM sodium chloride and 45 to 90 mM sodium citrate; containing SDS at the concentration of 0.1 to 1.0% by weight; containing nonspecific denatured DNA at the concentration of 0 to 200 μg/ml; which, as the case may be, may contain albumin, Ficoll, polyvinylpyrrolidone and the like at the concentration of 0 to 0.2% by weight, respectively (preferably, a hybridization solution containing 900 mM sodium chloride, 90 mM sodium citrate, 1.0% by weight SDS and 100 μg/ml denatured Calf-thymus DNA).

Following the hybridization, the membrane is removed, and washed with a washing liquid containing 15 to 300 mM sodium chloride, 1.5 to 30 mM sodium citrate and 0.1 to 1.0% by weight of SDS and the like at 42 to 65° C. (preferably, a washing liquid containing 15 mM sodium chloride, 1.5 mM sodium citrate and 1.0% by weight of SDS at 65° C.), or the like. Thus washed membrane is briefly rinsed with 2×SSC (300 mM sodium chloride, 30 mM sodium citrate), and thereafter dried. This membrane is subjected to, for example, autoradiography or the like to detect the position of the probe on the membrane. A clone corresponding to the position on the membrane of the DNA that hybridizes with the used probe is thereby specified on the original agar medium, and the clone having the DNA is isolated by picking it up.

The DNA of the gene of the present invention can be prepared from the cultured bacterial body obtained by the culturing thus obtained clone.

The DNA prepared in the manner as described above can be cloned into a vector in accordance with a method as described in "Molecular Cloning: A Laboratory Manual $2^{nd}$ edition" (1989), Cold Spring Harbor Laboratory Press, "Current Protocols in Molecular Biology" (1987), John Wiley & Sons, Inc. ISBN 0-471-50338-X and the like to obtain the recombinant vector of the present invention. Specific examples of the vector which may be used include pUC119 (manufactured by TAKARA SYUZO CO., LTD.), pTV118N (manufactured by TAKARA SYUZO CO., LTD.), pBluescriptII (manufactured by TOYOBO CO., LTD.), pCR2.1-TOPO (manufactured by Invitrogen Corporation), pTrc99A (manufactured by Pharmacia Corporation), pKK223-3 (manufactured by Pharmacia Corporation) and the like.

Furthermore, the nucleotide sequence of the aforementioned DNA can be analyzed by a dideoxy terminator method or the like described in Proceeding of Natural Academy of Science U.S.A. (1977) 74: 5463–5467 written by F. Sanger, S. Nicklen and A. R. Coulson, and the like. For preparing the sample for the analysis of nucleotide sequence, a commercially available reagent such as ABI PRISM Dye Terminator Cycle Sequencing Ready Reaction Kit of Perkin-Elmer Corporation or the like may be used.

The DNA obtained in the manner as described above encoding an amino acid sequence of a protein having an ability to reduce 2,2,2-trifluoroacetophenone to 2,2,2-trifluoro-1-phenylethanol can be confirmed as follows.

First, the DNA obtained in the manner as described above is inserted into a vector such that is linked downstream of a promoter which is operable in the host cell as described below, and this vector is introduced into a host cell to obtain a transformant. Then the culture of the transformant is allowed to contact with a ketone compound or an aldehyde compound. By analysis of the amount of 2,2,2-trifluoro-1-phenylethanol in the reaction product, the resultant DNA encoding an amino acid sequence of a protein having such an ability can be confirmed.

In order to allow the expression of the gene of the present invention in the host cell, for example, a gene in which a promoter operable in the host cell and the gene of the present invention are operatively linked is introduced into the host cell.

Herein, the term "operatively" means that when a host cell is transformed by introducing the aforementioned gene into the host cell, the present gene is bound to the promoter such that it is expressed under the control of the promoter.

Examples of the promoter include a promoter of lactose operon derived from *E. coli*, a promoter of tryptophan operon derived from *E. coli*, or synthetic promoters such as tac promoter, trc promoter and the like which are operable in *E. coli*. Also, promoters that control expression of the gene of the present invention in *Penicillium citrinum* may be utilized.

Specifically, a DNA fragment including the reductase gene of the present invention prepared by adding a DNA fragment that can be cleaved with EcoRI and a DNA fragment that can be cleaved with PstI to the 5' end and 3' end of the gene of the present invention, respectively, is made, and then, a DNA fragment including a gene obtained by subjecting the DNA fragment including the reductase gene of the present invention to a restriction enzyme treatment with restriction enzymes EcoRI and PstI to obtain a vector, and the vector obtained is bound with the vector pUC118 (manufactured byTAKARA SYUZO CO., LTD.), orpBluescriptII KS+(manufactured by TOYOBO CO., LTD.), or pTrc99A (manufactured by Pharmacia Corporation), or pKK223-3 (manufactured by Pharmacia Corporation) in a genetic engineering manner, thereby the reductase gene of the present invention is operatively linked to an operable promoter.

Generally, a recombinant vector, which is prepared by incorporating a gene operatively linked to a promoter operable in the host cell into the vector as described above, is introduced into the host cell. When a vector including a selective marker gene (for example, genes that impart antibiotic resistance such as kanamycin resistant gene, neomycin resistant gene, or the like) is used as the vector, a transformant into which the vector has been introduced can be selected by means of the phenotype of such a selective marker gene as the index.

Examples of the host cell into which the gene of the present invention operatively linked to a promoter operable in the host cell, or the recombinant vector of the present invention is introduced include microorganisms and the like belonging to genus *Escherichia*, genus *Bacillus*, genus *Corynebacterium*, genus *Staphylococcus*, genus *Streptomyces*, genus *Saccharomyces*, genus *Kluyveromyces* and genus *Aspergillus*, and the like.

The process for introducing the gene of the present invention operatively linked to a promoter operable in the host cell or the recombinant vector of the present invention into the host cell may be any method which is commonly used depending on the used host cell. Examples of the method include the calcium chloride method as described in "Molecular Cloning: A Laboratory Manual $2^{nd}$ edition" (1989), Cold Spring Harbor Laboratory Press, "Current Protocols in Molecular Biology" (1987), John Wiley &Sons, Inc. ISBN0-471-50338-X and the like, the electroporation method as described in "Methods in Electroporation: Gene Pulser/*E. coli* Pulser System" Bio-Rad Laboratories, (1993) and the like, and the like.

For selecting the transformant into which the gene of the present invention operatively linked to a promoter operable in the host cell, or the recombinant vector of the present invention has been introduced, the selection may be conducted employing the phenotype of the selective marker gene included in the vector as described above, as an index.

The fact that transformant possess the gene of the present invention can be confirmed by performing identification of the restriction site, analysis of the nucleotide sequence, Southern hybridization, Western hybridization and the like in accordance with the commonly used methods as described in "Molecular Cloning: A Laboratory Manual $2^{nd}$ edition" (1989), Cold Spring Harbor Laboratory Press and the like, for example.

Next, the protein of the present invention is illustrated.

The protein of the present invention has the amino acid sequence as described below.

(a) an amino acid sequence set out in SEQ ID NO: 1;

(b) an amino acid sequence having the sequence homology of 80% or more with the amino acid sequence set out in SEQ ID NO: 1, and the amino acid sequence is an amino acid sequence of a protein having at least an ability to reduce 2,2,2-trifluoroacetophenone to 2,2,2-trifluoro-1-phenylethanol;

(c) an amino acid sequence having the sequence homology of 90% or more with the amino acid sequence set out in SEQ ID NO: 1, and the amino acid sequence is an amino acid sequence of a protein having at least an ability to reduce 2,2,2-trifluoroacetophenone to 2,2,2-trifluoro-1-phenylethanol;

(d) an amino acid sequence encoded by a DNA having the nucleotide sequence set out in SEQ ID NO: 2;

(e) an amino acid sequence encoded by a DNA having the nucleotide sequence having the sequence homology of 80% or more with a DNA having the nucleotide sequence set out in SEQ ID NO: 2, and the amino acid sequence is an amino acid sequence of a protein having at least an ability to reduce 2,2,2-trifluoroacetophenone to 2,2,2-trifluoro-1-phenylethanol;

(f) an amino acid sequence encoded by a DNA that hybridizes under the stringent condition with a DNA having a nucleotide sequence which is complementary to the nucleotide sequence set out in SEQ ID NO: 2, and the amino acid sequence is an amino acid sequence of a protein having at least an ability to reduce 2,2,2-trifluoroacetophenone to 2,2,2-trifluoro-1-phenylethanol;

(g) an amino acid sequence of a protein obtained from a microorganism belonging to genus *Leifsonia*, and the amino acid sequence is an amino acid sequence of a protein having at least an ability to reduce 2,2,2-trifluoroacetophenone to 2,2,2-trifluoro-1-phenylethanol;

(h) an amino acid sequence of a protein obtained from *Leifsonia* sp. S-749, and the amino acid sequence is an amino acid sequence of a protein having at least an ability to reduce 2,2,2-trifluoroacetophenone to 2,2,2-trifluoro-1-phenylethanol The protein having the amino acid sequence set out in SEQ ID NO: 1 is aprotein also having an ability of the asymmetric reduction of 2,2,2-trifluoroacetophenone to produce (S)-2,2,2-trifluoro-1-phenylethanol predominantly. By allowing a transformant that produces the protein, or a processed product thereof to contact with a ketone compound, an optically active alcohol can be easily produced.

The protein of the present invention can be produced by, for example, culturing the transformant possessing the gene of the present invention.

As the medium used for culturing the transformant, for example, various culture medium containing a carbon source, a nitrogen source, organic salts, inorganic salts and the like which are commonly used for culturing host cells such as microorganisms can be used.

Examples of the carbon source include saccharides such as glucose, dextrin, sucrose; sugar alcohols such as glycerol; organic acids such as fumaric acid, citric acid, pyruvic acid; animal oils; vegetable oils; molasses. The amount of these carbon sources added to the culture medium is usually approximately 0.1 to 30% (w/v) with respect to the total medium volume.

Examples of the nitrogen source include natural organic nitrogen sources such as meat extract, peptone, yeast extract, malt extract, soybean powder, Corn Steep Liquor, cotton seed powder, dry yeast, casamino acids; amino acids; sodium salts of inorganic acids such as sodium nitrate; ammonium salts of inorganic acids such as ammonium chloride, ammonium sulfate, ammonium phosphate; ammonium salts of organic acids such as ammonium fumarate, ammonium citrate; and urea. Among them, ammonium salts of organic acids, natural organic nitrogen sources, amino acids and the like can be often used as a carbon source. The amount of these nitrogen sources added to the culture medium is usually approximately 0.1 to 30% (w/v) with respect to the total medium volume.

Examples of the organic salt and inorganic salt include chlorides, sulfates, acetates, carbonates and phosphates of potassium, sodium, magnesium, iron, manganese, cobalt, zinc and the like. Specific examples include sodium chloride, potassium chloride, magnesium sulfate, ferrous sulfate, manganese sulfate, cobalt chloride, zinc sulfate, copper sulfate, sodium acetate, calcium carbonate, potassium dihydrogenphosphate, dipotassium hydrogenphosphate and the like. The amount of these organic salts and/or inorganic salts added to the culture medium is usually approximately 0.0001 to 5% (w/v) with respect to the total medium volume.

Furthermore, in the case of a transformant into which a gene including the gene of the present invention operatively linked to a promoter of the allolactose-inducible type such as tac promoter, trc promoter, lac promoter or the like has been introduced, for example, a small amount of isopropyl thio-β-D galactoside (IPTG) may be added to the culture medium as an inducing agent for inducing the production of the protein of the present invention.

Cultivation of the transformant possessing the gene of the present invention may be performed in accordance with the commonly used methods for the cultivation of host cells such as microorganisms. Examples of the method include liquid cultivation such as test tube shaking cultivation, reciprocal shaking cultivation, Jar Fermenter cultivation, tank cultivation and the like, and solid cultivation.

Although the cultivation temperature may vary within the range that the transformant can grow, it is usually about 15 to 40° C. The pH of the cultivation medium is preferably in the range of about 6 to 8. Cultivation time varies depending on the cultivation condition. In general, cultivation time is preferably about 1 day to about 5 days.

As the method of the purification of the protein of the present invention from the culture of the transformant possessing the gene of the present invention, any method used for the purification of a protein may be employed, for example, the following method may be exemplified.

First, after collecting cells from the culture of the transformant by centrifugal separation or the like, the cells are disrupted by a physical disruption method such as sonication, DYNO-MILL treatment, French press treatment or the like, or a chemical disruption method in which a surfactant or a lytic enzyme such as lysozyme or the like is used. Cell free extract is prepared through removing impurities from the resulting disruption solution by centrifugal separation, filtrating with a membrane filter or the like. The obtained cell free extract is fractionated by using a separating purification method such as cation exchange chromatography, anion exchange chromatography, hydrophobic chromatography, gel chromatography or the like to purify the protein of the present invention.

Examples of carrier used for chromatography include insoluble high molecular carrier such as cellulose, dextrin, agarose and the like to which a carboxymethyl (CM) group, a diethylaminoethyl (DEAE) group, a phenyl group or a butyl group is introduced. Commercially available column packed with a carrier may be also used, and examples of the commercially available column packed with a carrier include e.g., Q-Sepharose FF, Phenyl-Sepharose HP (trade name, both manufactured by Amersham Pharmacia Biotech Corporation), TSK-gel G3000SW (trade name, manufactured by Tosoh Corporation), and the like.

For selecting the fraction containing the protein of the present invention, selection may be conducted with the ability of reducing 2,2,2-trifluoroacetophenone to 2,2,2-trifluoro-1-phenylethanol as an index.

In the present invention, an alcohol can be produced by allowing the aforementioned protein, a transformant that produces the protein or a processed product thereof to contact with a ketone compound or an aldehyde compound.

Examples of the ketone compound or aldehyde compound include propionaldehyde, n-butyl aldehyde, n-valeric aldehyde, n-hexyl aldehyde, n-heptyl aldehyde, n-decyl aldehyde, 2-oxopropionaldehyde, trans-cinnamic aldehyde, 4-bromobenzaldehyde, 2-nitrobenzaldehyde, 3-nitrobenzaldehyde, phenylacetoaldehyde, 4-chlorobenzaldehyde, 2-pentanone, 2-hexanone, 2-heptanone, 2-octanone, 2-nonanone, 3-pentanone, 3-chloro-2-butanone, tert-butyl acetoacetate, 4-hydroxy-2-butanone, hydroxyacetone, 1,1-dichloroacetone, chloroacetone, dihydroxyacetone, methyl 3-oxobutanoate, ethyl 3-oxabutanoate, ethyl 4-chloroacetoacetate, methyl 4-bromo-3-oxabutanoate, ethyl 4-bromo-3-oxabutanoate, N-tert-butoxycarbonyl-3-pyrrolidinone, isopropyl 4-cyano-3-oxobutanoate, ethyl 4-cyano-3-oxobutanoate, methyl 4-cyano-3-oxobutanoate, methyl 3-oxopentanoate, 2,2,2-trifluoroacetophenone, acetophenone, 2'-bromoacetophenone, 3'-bromoacetophenone, 4'-bromoacetophenone, 2-chloroacetophenone, 3'-chloroacetophenone, 4'-chloroacetophenone, benzyl acetone, 1-phenyl-2-butanone, m-methoxyacetophenone, 3,4-dimethoxyacetophenone, 4'-methoxyacetophenone, 2,3'-dichloroacetophenone, 3,4-dimethoxyphenyl acetone, cyclopentanone, 4-acetyl benzoic acid, D-(+)-glucose and the like.

It is preferred that the production of the alcohol described above is carried out in the presence of water and reduced nicotinamide adenine dinucleotide (hereinafter, abbreviated as NADH).

Water used in this method may be an aqueous buffer solution. Examples of the buffer agent used for this aqueous buffer solution include alkali metal salts of phosphoric acid such as sodium phosphate, potassium phosphate, alkali metal salts of acetic acid such as an aqueous sodium acetate solution, potassium acetate, and mixture thereof.

In the method described above, an organic solvent may be used in addition to water. Examples of the organic solvent include ethers such as t-butylmethyl ether, diisopropyl ether, tetrahydrofuran and the like; esters such as ethyl formate, ethyl acetate, propyl acetate, butyl acetate, ethyl propionate, butyl propionate and the like; hydrocarbons such as toluene, hexane, cyclohexane, heptane, isooctane and the like; alcohols such as methanol, ethanol, 2-propanol, butanol, t-butyl alcohol and the like; organic sulfur compounds such as dimethyl sulfoxide and the like; ketones such as acetone and the like; nitrites such as acetonitrile and the like, and mixture thereof.

The reaction in producing the alcohol as described above is performed by, for example, mixing such as stirring, shaking or the like, water, NADH, and a ketone compound or an aldehyde compound with the protein of the present invention, a transformant that produces the protein, or a processed product thereof. An organic solvent and the like can be added to the reaction system.

Although the pH upon the reaction may be selected appropriately, it is usually in the range of pH 3 to 10. Furthermore, although the reaction temperature may be selected appropriately, it is usually in the range of 0 to 60° C. from the standpoint of the stability of the raw material and product, and the reaction velocity.

End point of the reaction may be determined by, for example, monitoring the amount of the ketone compound or the aldehyde compound in the reaction mixture by liquid chromatography or the like. Although the reaction time may be selected appropriately, it is usually in the range of from 0.5 hours to 10 days.

Recovery of the alcohol from the reaction mixture may be carried out by an arbitrary known process. Example of the process include processes in which purification is carried out in combination with a treatment such as extraction with an organic solvent, concentration operation of the reaction mixture, if necessary, column chromatography, distillation or the like.

The protein of the present invention, a transformant that produces the same or a processed product thereof can be used for the production of an alcohol as described above in a variety of forms.

Examples of the form include cultures of the transformant possessing the gene of the present invention, processed products of the transformant, cell free extracts, purified crude proteins, purified proteins and the like, and immobilized products of the same. Examples of the processed product of the transformant include lyophilized transformant, transformant treated with an organic solvent, dried transformant, disrupted transformant, self digestion product of the transformant, ultrasonication product of the transformant, extract of the transformant, and alkaline treatment product of the transformant. In addition, examples of the process for obtaining the immobilized product include carrier binding processes (process in which the protein or the like of the present invention is adsorbed to an inorganic carrier such as silica gel, ceramic or the like, cellulose, an ion exchange resin, or the like) and entrapment (process in which the protein or the like of the present invention is trapped into the net structure of polymers such as polyacrylamide, sulfur-containing polysaccharide gel (for example, carrageenan gel), alginic acid gel, agar gel and the like).

Taking into account of industrial production of the transformant that possesses the gene of the present invention, the method in which a processed product using a killed transformant is preferable to a living transformant, from the standpoint of less limitation of the manufacturing facilities. Examples of the method of the killing treatment include physically sterilizing methods (heating, drying, freezing, irradiation of rays, ultrasonic wave, filtration, electrification), and sterilizing methods using a chemical (e.g., alkalis, acids, halogens, oxidizing agents, sulfur, boron, arsenic, metals, alcohols, phenols, amines, sulfides, ethers, aldehydes, ketones, cyans and antibiotics). Among these sterilizing methods, it is preferred to select a method of the killing treatment which results in inactivation of the enzyme activity of the protein of the present invention as little as possible, and is unlikely to cause influences such as a residence and contamination in the reaction system.

Moreover, according to the present invention, production of the alcohol is usually carried out in the presence of NADH. The NADH is converted into oxidized β-nicotinamide adenine dinucleotide (hereinafter, described as $NAD^+$ accompanied with the progress of the reductive reaction of the ketone compound or aldehyde compound. As the $NAD^+$ generated by the conversion can be restored to the original NADH by a protein having an ability to convert $NAD^+$ into reduced (NADH), a protein having an ability to convert $NAD^+$ into NADH is preferably co-existed in the aforementioned reaction system.

Examples of the protein having an ability to convert $NAD^+$ into NADH include glucose dehydrogenase, alcohol dehydrogenase, aldehyde dehydrogenase, amino acid dehydrogenase, organic acid dehydrogenase (malate dehydrogenase and the like), and the like.

When the protein having an ability to convert $NAD^+$ into NADH is glucose dehydrogenase, there may be cases in which coexistence of glucose or the like in the reaction system enhances the activity of the protein. Therefore, glucose or the like may be added to, for example, the reaction mixture.

The protein may coexist in the reaction system in the form of the enzyme itself, or the microorganism having the enzyme or the processed product of such a microorganism. A transformant including a gene having a nucleotide sequence encoding the amino acid sequence of the protein having an ability to convert $NAD^+$ into NADH, or the processed product of the same may co-exist in the reaction system. The processed product herein means similar ones to the "processed product of the transformant" as described above.

In the production of the alcohol according to the present invention, it may be also carried out using a transformant concomitantly possessing a gene having a nucleotide sequence encoding an amino acid sequence of a protein having an ability to convert $NAD^+$ into NADH such as glucose dehydrogenase, alcohol dehydrogenase, aldehyde dehydrogenase, amino acid dehydrogenase, organic acid dehydrogenase (malate dehydrogenase or the like), or the like.

Examples of the process for introducing both genes into the host cell include processes in which a single vector including both genes is introduced into the host cell, processes in which the host cell is transformed with recombinant vectors in which both genes are separately introduced to multiple vectors having the different origin of replication, and the like. Further, either one gene or both genes may be introduced into the chromosome of the host cell.

In the process for introducing a single vector including both genes into a host cell, for example, a recombinant vector may be constructed by linking a region regarding the control of expression such as promoter, terminator or the like to both genes, respectively, ora recombinant vector may be constructed which allows expression as an operon including multiple cistrons such as lactose operon.

EXAMPLES

The present invention is described in more detail by way of Examples, which should not be construed as a limitation upon the scope of the present invention.

Example 1

Preparation of the Protein of the Present Invention, and Obtaining the Gene of the Present Invention and Analysis Thereof (1) Preparation of the Protein of the Present Invention In a 5 L jar fermenter was charged 3 L of a medium (prepared by dissolving 3 g/L of $(NH_4)_2SO_4$, 3 g/L of $K_2HPO_4$, 1 g/L of NaCl, 0.2 g/L of $MgSO_4.7H_2O$, 2 g/L of DL-Phenylethyl Alcohol, 0.5 g/L of Antifoam PE-H (manufactured by Wako Pure Chemical Industries, Ltd) in water followed by adjusting the pH of 7.0) and sterilized at 121° C. for 15 min. Then, 30 ml of a cultivation fluid of *Leifsonia* sp. S-749 strain which had been cultured (30° C., 18 hours, shaking cultivation) in a medium prepared by dissolving 5 g/L of Bacto Peptone and 5 g/L of Yeast Extract in water followed by adjusting the pH of 7.0 was added to the aforementioned jar fermenter, and cultured using the jar fermenter at 30° C. for 48 hours. Thereafter, about 5.0 g of the wet bacterial bodies were obtained as a precipitate by centrifugal separation (8000×g, 10 min) of thus resulting cultivation fluid.

About 10.0 g of the wet bacterial bodies of thus prepared *Leifsonia* sp. S-749 strain were suspended in 80 ml of 20 mM Tris-HCl buffer (pH 7.0), and subjected to an ultrasonic disruption using ULTRASONIC DISRUPTOR UD-200 (manufactured by TOMY Corporation), while ice-cooling with OUTPUT8 for 3 minutes. A centrifugal supernatant liquid (about 85 ml) was obtained by the centrifugal separation of thus resulting disruption liquid (4° C., 15000 rpm, for 30 min.).

After gradually adding ammonium sulfate until the concentration of 144 g/L (25% saturation) to thus resulting centrifugal supernatant liquid (about 85 ml), a centrifugal supernatant liquid (about 90 ml) was obtained by the centrifugal separation (4° C., 15000 rpm, for 30 min). After gradually adding ammonium sulfate until the concentration of 390 g/L (60% saturation) to thus resulting centrifugal supernatant liquid (about 90 ml), centrifugal separation (4° C., 15000 rpm, for 30 min) was conducted. Thus resulting precipitate was dissolved in 20 ml of 20 mM Tris-HCl buffer (pH 7.0) to obtain a 22 ml precipitate solution. The precipitate solution was charged in DIALYSIS MEMBRANE SIZE8 (manufactured by WAKO), and dialyzed over 20 mM Tris-HCl buffer (pH 7.0) at 4° C. overnight. The obtained solution was loaded on DEAE-TOYOPEARL (manufactured by Amersham Pharmacia Biotech Corporation), which had been equilibrated with Tris-HCl buffer (20 mM, pH 7.0), and eluted with Tris-HCl buffer including sodium chloride dissolved therein (with the concentration gradient of sodium chloride concentration of 0 M to 1.0 M) as a mobile phase to obtain an eluate fraction having the reductase activity (18 ml).

To this eluate fraction (18 ml) was added ammonium sulfate of 1.3 M, and after stirring in ice for 30 min, the mixture was subjected to centrifugal separation (4° C., 15000 rpm, for 30 min). The centrifugal supernatant liquid (29 ml) was loaded on BUTYL-TOYOPEARL (manufactured by Amersham Pharmacia Biotech Corporation), which had been equilibrated with Tris-HCl buffer (20 mM, pH 7.0)+1.3 M ammonium sulfate, and eluted with Tris-HCl buffer including sodium sulfate dissolved therein (with the concentration gradient of sodium sulfate concentration of 1.3 M to 0 M) as a mobile phase to obtain an eluate fraction having the reductase activity (31 ml). After gradually adding ammonium sulfate until the concentration of 472 g/L (70% saturation) to thus resulting eluate fraction (31 ml), the mixture was subjected to centrifugal separation (4° C., 15000 rpm, for 30 min). Thus resulting precipitate was dissolved in 1 ml of 20 mM Tris-HCl buffer (pH 7.0) to give about a 1 ml precipitate lysis solution. This precipitate solution in an amount of 1 ml was charged in DIALYSIS MEMBRANE SIZE8 (manufactured by WAKO), and dialyzed over 20 mM Tris-HCl buffer (pH 7.0) at 4° C. overnight to give the dialysate (about 3 ml). This dialysate (about 3 ml) was loaded on Cellulofine GCL-2000sf (manufactured by Amersham Pharmacia Biotech Corporation), which had been equilibrated with Tris-HCl buffer (20 mM, pH 7.0), and the eluate fraction (9.7 ml) having the reductase activity was obtained by charging Tris-HCl buffer at a flow rate of 0.3 ml/min. Thus resulting eluate fraction (9.7 ml) was loadedonBioassistQ (manufactured by Amersham Pharmacia Biotech Corporation), which had been equilibrated with Tris-HCl buffer (20 mM, pH 7.0), and eluted with Tris-HCl buffer including sodium chloride dissolved therein (with the concentration gradient of sodium chloride concentration of 0 M to 0.8 M) as a mobile phase to obtain an eluate fraction having the reductase activity (1 ml). Thus resulting eluate fraction (1 ml) was subjected to gel filtration [column: TSK-GEL G3000SWXL (manufactured by Amersham Pharmacia Biotech Corporation)] [mobile phase: BIS-TRIS-PROPANE buffer (20 mM, pH 7.0)], to obtain an eluate fraction having the reductase activity (1 ml: corresponding to the segment with the molecular weight of about 110,000 Dalton) as a purified enzyme liquid.

Reductase activity was measured on the eluate fraction obtained by the chromatography and the like according to the following procedure.

To a phosphate buffer (50 mM, pH 7.0) including 2,2,2-trifluoroacetophenone (2 mM) and NADH (0.27 mM) dissolved therein was added the eluate fraction obtained by the chromatography or the like to give the total volume of 1.5 ml. After incubating this mixture at 25° C. for 20 sec, absorbance at 340 nm was measured. Amount of consumption of NADH was calculated from the absorbance at 340 nm to estimate the reductase activity of the eluate fraction.

(2) Analysis of Amino Acid Sequence of Partial Peptide Derived from the Protein of the Present Invention The active fraction (A) obtained by the procedure as described above was subjected to SDS polyacrylamide gel electrophoresis in accordance with the method described in Laemmli, U. K., Nature, (1970) 227, 680. The gel after electrophoresis was stained with a Coomassie Brilliant Blue G250 staining solution (manufactured by BIO-RAD), and the gel in the stained part was cut off. This gel was subjected to reducing alkylation using dithiothreitol and acetamide iodide followed by a treatment with trypsin. Thereafter, the peptide was extracted from the gel. Thus extracted peptide was fractionated on HPLC (column: TSK gel ODS-80Ts QA, 2.0 mm×250 mm (Tosoh Corporation),
solvent A: 0.1% TFA(Trifluoro acetic acid)
solvent B: 0.09% TFA in 90% acetonitrile
flow rate: 200 µL/min
temperature: room temperature(25° C.)
detection: 210 nm, 280 nm
gradient

| 0 (min) | 0 (%) |
|---|---|
| 2 | 0 |
| 7 | 10 |
| 82 | 50 |
| 87 | 100 |
| 92 | 100 |
| 97 | 0 | fractionate aliquot: 200 µL/Fraction.

Each fraction thus fractionated was sequenced with a protein sequencer (Procise 494HT Protein Sequencing System).

Each amino acid sequence thus determined is set out in SEQ ID NO: 5 (N terminal amino acid sequence (AQYDVADRSAIVTGG)) and SEQ ID NO: 6 (internal amino acid sequence (IAVNNAGIGGEA)), respectively.

(3) Analysis of Partial Nucleotide Sequence Derived from the Gene of the Present Invention Oligonucleotide primers having the nucleotide sequence set out in SEQ ID NO: 7 (TFAR-F (CARTAYGAYGTIGC-NGAHMG) and SEQ ID NO: 8 (TFAR-R(CCDATIC-CNGCRTTRTTNAC) were synthesized on the basis of the amino acid sequence set out in SEQ ID NO: 5. Herein, R as a base means G or A; Y means T or C; I means inosine; N means A or C or G or T; H means A or C or T; M means A or C; and D means A or G or T.

The PCR reaction was performed using the oligonucleotide primers having the nucleotide sequences set out in SEQ ID NO: 7 and 8, and *Leifsonia* sp. DNA as a template, with the following composition of the reaction mixture and under the following reaction condition.

[Composition of Reaction Mixture]

| *Leifsonia* sp. DNA | 1 µl |
|---|---|
| dNTP (each 2.5 mM-mix) | 2 µl |
| primers (50 µM) | each 2 µl |
| 10 × EX Taq buffer (with MgCl$_2$) | 2 µl |
| TaKaRa Ex Taq (5 U/µl) | 0.5 µl |
| ultra pure water | 10.5 µl |

[Reaction Condition]

A vessel charged with the reaction mixture having the aforementioned composition was placed in the PERKIN ELMER-GeneAmp PCR System 2400. After heating at 94° C. for 5 min, a cycle of at 94° C. for 0.5 min, at 55° C. for 0.5 min and at 72° C. for 0.5 min was repeated 30 times, followed by additional incubation at 72° C. for 10 min.

Thereafter, the PCR product was ligated with pGEM-T Easy Vector System I (manufactured by PROMEGA Corporation), and E. coli XL-1 Blue MRF' strain was transformed with thus obtained ligation liquid.

To an LB (1% bacto-triptone, 0.5% bacto-yeast extract, 1% sodium chloride) medium containing 50 μg/ml ampicillin was inoculated thus obtained transformant, and was cultured. A plasmid was collected from the culture bacterial bodies using QIAprep Spin Miniprep Kit (manufactured by Qiagen Corporation).

Analysis of the nucleotide sequence of the DNA fragment inserted into the plasmid was performed through the analysis of the nucleotide sequence of thus obtained DNA with ABI PRISM 310 Genetic Analyzer (manufactured by ABI Corporation). The nucleotide sequence of the DNA fragment inserted into the plasmid is set out in SEQ ID NO: 9.

(4) Analysis of Nucleotide Sequence of the Gene of the Present Invention

Ligation between a Leifsonia DNA partially degraded with Sau3A I and cosmid vector pWE15 cleaved with BamHI was carried out.

In vitro packaging was executed using Gigapack Gold III (manufactured by STRATAGENE Corporation).

After the infection of E. coli XL1-Blue MRF' with the phage followed by culturing in the LB plate containing ampicillin, the cells were collected, and the cosmid was extracted by an alkali SDS method.

After introducing the cosmid into E. coli XL1-Blue MRF' and culturing in the LB plate containing ampicillin, blotting on a nylon membrane was carried out.

Preparation of a labelled probe and colony hybridization were performed according to the protocol of Alkphos Direct Labelling Reagents (Amersham Bioscience Inc.). Condition in the colony hybridization was: prehybridization at 75° C., hybridization at 75° C., and first washing buffer at 75° C. The nucleotide sequence of the DNA fragment used as the probe is set out in SEQ ID NO: 10.

Detection was conducted by the exposure on an X-ray film using a CDP-Star Detection reagent.

Analysis of the nucleotide sequence of the DNA fragment inserted into the plasmid was carried out by analyzing the nucleotide sequence of the resulting DNA with ABI PRISM 310 Genetic Analyzer (manufactured by ABI Corporation). The nucleotide sequence of the DNA fragment inserted into the plasmid is set out in SEQ ID NO: 2.

Example 2

Preparation of the Vector of the Present Invention, Production of the Transformant of the Present Invention and Example of Reductive Reaction (Part 1)

(1) Preparation of Leifsonia sp. DNA

Leifsonia sp. S-749 strain was cultured in 100 ml of the sterilized PY medium (peptone, yeast extract each 0.5%, pH 7.0) at 30° C. overnight. Chromosomal DNA was purified from the bacterial bodies using Qiagen Genomic Tip (manufactured by Qiagen Corporation), in accordance with the method described in the manual attached thereto.

(2) Preparation of the Vector of the Present Invention

An oligonucleotide primer having the nucleotide sequence set out in SEQ IN NO: 11 and an oligonucleotide primer having the nucleotide sequence set out in SEQ IN NO: 12 were synthesized on the basis of the nucleotide sequence set out in SEQ ID NO: 2.

The PCR reaction was performed using the oligonucleotide primer having the nucleotide sequence set out in SEQ ID NO: 11 and the oligonucleotide primer having the nucleotide sequence set out in SEQ ID NO: 12 as primers, and the chromosomal DNA of Leifsonia sp. as a template, with the following composition of the reaction mixture and under the following reaction condition.

[Composition of Reaction Mixture]

| | |
|---|---|
| Leifsonia sp. chromosomal DNA | 1 μl |
| dNTP (each 2.5 mM-mix) | 2 μl |
| primers (50 μM) | each 2 μl |
| 10 × EX Taq buffer (with MgCl$_2$) | 2 μl |
| TaKaRa Ex Taq (5 U/μl) | 0.5 μl |
| ultra pure water | 10.5 μl |

[Reaction Condition]

A vessel charged with the reaction mixture having the aforementioned composition was placed in the PERKIN ELMER-GeneAmp PCR System 2400. After heating at 94° C. for 5 min, a cycle of at 94° C. for 0.5 min, at 55° C. for 0.5 min and at 72° C. for 0.5 min was repeated 30 times, followed by additional incubation at 72° C. for 10 min.

Thereafter, two kinds of restriction enzymes (NcoI and PstI) were added to the PCR reaction mixture to achieve double digestion of the DNA fragment. Then, the DNA fragment digested with the enzymes was purified.

On the other hand, the plasmid vector pTrc99A (manufactured by Pharmacia Corporation) was subjected to double-digestion with two kinds of restriction enzymes (NcoI and PstI), and the DNA fragment digested with the enzymes was purified. These DNA fragments digested with enzymes were mixed, and ligated with T4 DNA ligase. Then, E. coli XL1-Blue MRF' was transformed with thus resulting ligation liquid. A plasmid containing the reductase gene of the present invention (hereinafter, may be also referred to as plasmid pTrcTFAR) was collected from the resulting transformant using QIAprep Spin Miniprep Kit (manufactured by Qiagen Corporation).

(3) Preparation of the Transformant of the Present Invention and Example of Reductive Reaction To the sterilized LB medium (4 ml) containing 0.4 mM IPTGand 100 μg/ml ampicillin was inoculated thus resulting transformant, and was subjected to the shaking cultivation (30° C., 24 hours). Thus resulting cultivation fluid was subjected to centrifugal separation to obtain wet bacterial bodies of 0.02 g.

To 0.02 g of the aforementioned wet bodies was added 500 μl of 50 mM phosphate buffer (pH 7.0) containing 1% 2,2,2-trifluoroacetophenone and 5% 2-propanol, followed by stirring at 30° C. for 18 hours. Then, after adding 500 μl of ethyl acetate to the reaction mixture, the mixture was subjected to centrifugal separation to obtain the organic phase. The organic phase was subjected to an analysis of the content by way of gas chromatography under the following condition. 2,2,2-Trifluoro-1-phenylethanol was produced at a ratio of 49.4% based on the amount of 2,2,2-trifluoroacetophenone used in the reaction. Furthermore, optical purity of 2,2,2-trifluoro-1-phenylethanol in the organic phase was measured under the following condition. The (S)-form of 99% e.e. was demonstrated.

By concentrating the organic phase, crude (S)-2,2,2-trifluoro-1-phenylethanol is obtained. (Condition of gas chromatography)
column: Cyclodextrine-β-236M-19 (0.25 mm×25 M, DF)
column temperature: 140° C.
carrier gas: helium (flow rate: 1 ml/min.)
detector: FID Absolute configuration of the product was determined by comparison with the authentic sample of (S)-2,2,2-trifluoro-1-phenylethanol.
Retention time: Trifluoroacetophenone (2.3 min),
(S)-2,2,2-trifluoro-1-phenylethanol (6.9 min),
(R)-2,2,2-trifluoro-1-phenylethanol (7.1 min)

Example 3

Production Example of Alcohol Using Ketone Compound or Aldehyde Compound as Raw Material (part 1: Example of Reductive Reaction Using the Microorganism of the Present Invention)

*Leifsonia* sp. S-749 strain was cultured in the PY medium (peptone, yeast extract each 0.5%, pH 7.0) at 30° C. overnight. Thus resulting cultivation fluid in an amount of 0.1 ml was applied on a plate medium having the composition described below, and cultured at 30° C. for 3 days under a styrene-saturated condition (using the Duhrum fermentation tube).

[Composition of Culture Fluid]

| | | |
|---|---|---|
| $(NH_4)_2SO_4$ | 0.3% | |
| $KH_2PO_4$ | 0.3% | |
| NaCl | 0.1% | |
| $MgSO_4 \cdot 7H_2O$ | 0.02% | |
| Agar Powder | 1.5% | |
| Yeast Extract | 0.1% | |
| Tap water | | |
| pH 7.0 | | |

To the plate medium was added 2 ml of 20 mM phosphate buffer (pH 7.0) per one plate, and the bacterium was scraped off using a spreader. Thereafter, the cells were charged in a 2 ml Eppendorf tube, and subjected to centrifugal separation (4° C., 15000 rpm, 1 min.). To the pellet of the bacterial bodies obtained after removing the supernatant was added 1 ml of the following reaction mixture to carry out a resting bacterial reaction at 30° C. for 18 hours using the Bio Shaker.

[Composition of Reaction Mixture]

| | |
|---|---|
| 50 mM | phosphate buffer (pH 7.0) |
| 3% | 2-propanol |
| 20 mM | 2,2,2-trifluoroacetophenone |
| 0.5 mM | $NAD^+$ |
| 0.5 mM | $NADP^+$ |

After adding 1 ml of ethyl acetate to the reaction mixture followed by vortex, the mixture was subjected to centrifugal separation (4° C., 15000 rpm, 10 min.). The organic phase was subjected to an analysis of content and an analysis of optical isomer by way of gas chromatography under the following condition. 2,2,2-Trifluoro-1-phenylethanol was produced at a ratio of 100% based on the amount of 2,2,2-trifluoroacetophenone used in the reaction. Optical purity of 2,2,2-trifluoro-1-phenylethanol was measured, the (S)-form of equal to or greater than 99.9% e.e. was demonstrated.

By concentrating the organic phase, crude (S)-2,2,2-trifluoro-1-phenylethanol was obtained. (Condition of gas chromatography)
column: Cyclodextrine-β-236M-19 (0.25 mm×25 M, DF)
column temperature: 140° C.
carrier gas: helium (flow rate: 1 ml/min.)
detector: FID Absolute configuration of the product was determined by the comparison with the authentic sample of (S)-2,2,2-trifluoro-1-phenylethanol.
Retention time: Trifluoroacetophenone (2.3 min),
(S)-2,2,2-trifluoro-1-phenylethanol (6.9 min),
(R)-2,2,2-trifluoro-1-phenylethanol (7.1 min)

Example 4

Production Example of Alcohol Using Ketone Compound or Aldehyde Compound as Raw Material (Part 2: Example of a Reductive Reaction Using the Protein of the Present Invention)

An alcohol was produced from a ketone compound or an aldehyde compound using the purified enzyme liquid obtained in Example 1. The results are described below.

The reducing activity was measured as follows.

To a phosphate buffer (50 mM, pH 7.0) including the substrate (2 mM) and NADH (0.27 mM) dissolved therein was added the purified enzyme liquid to give the total volume of 1.5 ml. After incubating this mixture at 25° C. for 20 sec, absorbance at 340 nm was measured. Amount of consumption of NADH was calculated from the absorbance at 340 nm to estimate the reductase activity.

(Results)

In the order of the compound/concentration (mM)/reductase activity (U/mL): propionaldehyde/2/2, n-butyl aldehyde/2/8, n-valeric aldehyde/2/108, n-hexyl aldehyde/2/844, n-heptyl aldehyde/2/619, n-decyl aldehyde/2/394, 2-oxopropionaldehyde/2/5, trans cinnamic aldehyde/2/212, 4-bromobenzaldehyde/2/47, 2-nitrobenzaldehyde/2/48, 3-nitrobenzaldehyde/2/25, phenylacetoaldehyde/2/7, 4-chlorobenzaldehyde/2/20, 2-pentanone/2/14, 2-hexanone/2/85, 2-heptanone/2/188, 2-octanone/2/121, 2-nonanone/2/90, 3-pentanone/2/2, 3-chloro-2-butanone/2/124, tert-butyl acetoacetate/2/466, 4-hydroxy-2-butanone/2/21, hydroxyacetone/2/8, 1,1-dichloroacetone/2/884, chloroacetone/2/195, dihydroxyacetone/2/2, 1,1-dichloroacetone/2/2, methyl 3-oxobutanoate/2/107, ethyl 3-oxabutanonate/2/253, ethyl 4-chloroacetoacetate/2/663, methyl 4-bromo-3-oxabutanoate/2/135, ethyl 4-bromo-3-oxabutanoate/2/419, N-tert-butoxycarbonyl-3-pyrrolidinone/2/4, isopropyl 4-cyano-3-oxobutanoate/2/2, ethyl 4-cyano-3-oxobutanoate/2/4, methyl 4-cyano-3-oxobutanoate/2/4, methyl 3-oxopentanoate/2/14, 2,2,2-trifluoroacetophenone/2/82, acetophenone/2/5, 2'-bromoacetophenone/2/2, 3'-bromoacetophenone/2/124, 4'-bromoacetophenone/2/63, 2-chloroacetophenone/2/2, 3'-chloroacetophenone/2/57, 4'-chloroacetophenone/2/49, benzyl acetone/2/289, 1-pheny-2-butanone/2/10, m-methoxyacetophenone/2/42, 3,4-dimethoxyacetophenone/2/20, 4'-methoxyacetophenone/2/3, 2,3'-dichloroacetophenone/2/27, 3,4-dimethoxyphenyl acetone/2/16, cyclopentanone/2/1, 4-acetyl benzoic acid/2/2, D-(+)-glucose/2/1.

Example 5

Production Example of Ketone Compound or Aldehyde Compound Using Alcohol as Raw Material (Example of Oxidative Reaction Using the Protein of the Present Invention)

A ketone compound or an aldehyde compound was produced from an alcohol using the purified enzyme liquid obtained in Example 1. The results are described below.

The oxidizing activity was measured as follows.

To a phosphate buffer (50 mM, pH 7.0) including the substrate (10 mM) and NAD$^+$ (3 mM) dissolved therein was added the purified enzyme liquid to give the total volume of 1.5 ml. After incubating this mixture at 25° C. for 20 sec, absorbance at 340 nm was measured. Amount of production of NADH was calculated from the absorbance at 340 nm to estimate the oxidase activity.

(Results)

In the order of the compound/concentration (mM)/oxidase activity (U/mL): 1-heptanol/10/7, 1-octanol/5/4, 2-propanol/10/12, (R)-2-butanol/10/33, (R)-2-pentanol/10/80, (R,S)-2-pentanol/10/38, (R)-2-hexanol/10/270, (R,S)-2-hexanol/10/179, (S)-(+)-2-heptanol/10/20, (R)-(−)-2-heptanol/10/415, (R,S)-2-heptanol/10/277, 3-heptanol/10/11, (S)-(+)-2-octanol/5/4, (R)-(−)-2-octanol/5/181, cyclopentanol/10/2, (R)-(+)-1-phenylethanol/10/10, 2-phenylethanol/10/2, cinnamyl alcohol/10/6.

Example 6

Preparation of Plasmid Containing the Reductase Gene of the Present Invention and Coenzyme Regenerating Gene: Construction of Plasmid pTrcTFARSbG (6-1) Provision for Preparing Gene Having Nucleotide Sequence Encoding Amino Acid Sequence of Enzyme Having Ability to Convert Oxidized β-Nicotinamide Adenine Dinucleotide to the Reduced Form The LB medium (1% triptone, 0.5% yeast extract, 1% sodium chloride) in an amount of 100 ml was charged in a flask, and sterilized. To thus prepared medium was inoculated 0.3 ml of a cultivation fluid in which *Bacillus megaterium* IFO12108 strain had been previously cultured in a liquid medium having the aforementioned composition, and the mixture was subjected to shaking cultivation at 30° C. for 10 hours.

After the cultivation, the bacterial bodies were collected by centrifugal separation (15000×g, 15 min, 4° C.) of the resulting cultivation fluid. Thus collected bacterial bodies were suspended in 30 ml of 50 mM potassium dihydrogenphosphate—dipotassium hydrogenphosphate buffer (pH 7.0). This suspension was subjected to centrifugal separation (15000×g, 15 min, 4° C.) to obtain washed bacterial bodies. Chromosomal DNA was purified from the washed bacterial bodies using Qiagen Genomic Tip (manufactured by Qiagen Corporation), in accordance with the method described in the manual attached thereto.

(6-2) Preparation of Gene Having Nucleotide Sequence Encoding Amino Acid Sequence of Enzyme Having Ability to Convert Oxidized β-Nicotinamide Adenine Dinucleotide to the Reduced Form.

An oligonucleotide having the nucleotide sequence set out in SEQ IN NO: 13 and an oligonucleotide having the nucleotide sequence set out in SEQ IN NO: 14 are synthesized on the basis of the amino acid sequence of glucose dehydrogenase derived from known *Bacillus megaterium* IWG3 described in The Journal of Biological Chemistry Vol. 264, No. 11, 6381–6385 (1989).

The PCR reaction is performed using the oligonucleotide having the nucleotide sequence set out in SEQ ID NO: 13 and the oligonucleotide having the nucleotide sequence set out in SEQ ID NO: 14 as primers, and the chromosomal DNA purified in the aforementioned (6-1) as a template, with the composition of the reaction mixture and under the reaction condition as described in Example 2 (2-2).

By adding two kinds of restriction enzymes (PstI and HindIII) to the PCR amplified DNA fragment obtained by purifying the PCR reaction mixture, the PCR amplified DNA fragment is double-digested. Then the digested DNA fragment is purified.

On the other hand, by adding two kinds of restriction enzymes (PstI and HindIII) to the plasmid pTrcTFAR prepared in Example 2, the plasmid is double-digested. Then thus resulting DNA fragment is purified.

Two kinds of DNA fragments obtained by purification in the above manner are mixed, and ligated using T4 DNA ligase. *E. coli* DH5α is transformed with thus resulting ligation liquid.

A plasmid containing the reductase gene and the coenzyme regenerating gene of the present invention (hereinafter, may be also referred to as plasmid pTrcTFARSbG) is collected from the resulting transformant using QIAprep Spin Miniprep Kit (manufactured by Qiagen Corporation).

In addition, after executing a sequencing reaction using Dye Terminator Cycle sequencing FS ready Reaction Kit (manufactured by Perkin-Elmer) with the PCR amplified DNA fragment as a template, the nucleotide sequence of thus obtained DNA is analyzed with the DNA sequencer 373A (manufactured by Perkin-Elmer).

Example 7

Preparation of Transformant Containing the Reductase Gene and Coenzyme Regenerating Enzyme Gene of the Present Invention

*E. coli* HB101 is transformed with the plasmid pTrcTFARSbG prepared in Example 6. After inoculating thus resulting transformant into the sterilized LB medium (100 ml×3 tubes) containing 0.4 mM IPTG, 0.01% (W/V) ZnCl$_2$ and 50 µg/ml ampicillin, the mixture is subjected to shaking cultivation (30° C., 18 hours). After the cultivation, washed bacterial bodies are collected by conducting the centrifugal separation and washing of the cultivation fluid.

Example 8

Method for Producing (S)-2,2,2-trifluoro-1-phenylethanol (part 1)

To 20 ml of 50 mM potassium dihydrogenphosphate-dipotassium hydrogenphosphate buffer (pH 7.0) are added 1 g of the washed bacterial bodies prepared in Example 7, 12 mg of NAD+ and 2.5 g of glucose. After adding 240 mg of 2,2,2-trifluoroacetophenone to this mixture, the pH of this mixture is adjusted to 7.0 with a 15% aqueous sodium carbonate solution. The reaction is executed by stirring thus obtained mixture (reaction mixture) at 30° C. for 4 hours. After completion of the reaction, 25 ml of ethyl acetate is poured into the reaction mixture and stirred, followed by centrifugal separation for separately collecting the organic phase and the aqueous phase. To the collected aqueous phase is added 25 ml of ethyl acetate again, and the similar operation is repeated. After concentrating the combined organic phase obtained in such a manner, the concentrate is dissolved in 30 ml of chloroform and dried using anhydrous $Na_2SO_4$. After drying, chloroform is distilled off to obtain (S)-2,2,2-trifluoro-1-phenylethanol.

Example 9

Process for Obtaining Microorganism that Produces the Reductase of the Present Invention (1) Preparation of Washed Bacterial Bodies After inoculating a commercially available microorganism, or a microorganism isolated from soil or the like to the sterilized LB medium (10 ml), it is subjected to shaking cultivation (30° C., 18 hours). After the cultivation, washed bacterial bodies are collected by conducting the centrifugal separation and washing of the cultivation fluid.

(2) Screening

To 20 ml of 100 mM potassium dihydrogenphosphate-dipotassium hydrogenphosphate buffer (pH 6.5) are added 1 g of the washed bacterial bodies prepared in the aforementioned (9-1), 12 mg of $NADP^+$, 12 mg of $NAD^+$ and 2.5 g of glucose. After adding 240 mg of 2,2,2-trifluoroacetophenone to the mixture, the pH of the mixture is adjusted to 6.5 with a 15% aqueous sodium carbonate solution. The reaction is executed by stirring thus obtained mixture (reaction mixture) at 30° C. for 4 hours. After completion of the reaction, 25 ml of ethyl acetate is poured into the reaction mixture and stirred, followed by centrifugal separation for separately collecting the organic phase and the aqueous phase. To the collected aqueous phase is added 25 ml of ethyl acetate again, and the similar operation is repeated. After concentrating the combined organic phase obtained in such a manner, the concentrate is dissolved in 30 ml of chloroform and dried using anhydrous $Na_2SO_4$. After drying, chloroform is distilled off to obtain a residue. 2,2,2-Trifluoro-1-phenylethanol in the obtained residue is confirmed by a qualitative and/or quantitative analysis by way of gas chromatography.

According to the present invention, a gene encoding a protein having an excellent catalytic ability for producing an alcohol from a ketone compound or an aldehyde compound, said protein, and a method for producing an alcohol utilizing the same can be provided.

[Sequence Listing Free Text]
SEQ ID NO: 3
  Oligonucleotide primer which is designed for PCR
SEQ ID NO: 4
  Oligonucleotide primer which is designed for PCR
SEQ ID NO: 7
  Oligonucleotide primer which is designed for PCR
SEQ ID NO: 8
  Oligonucleotide primer which is designed for PCR
SEQ ID NO: 11
  Oligonucleotide primer which is designed for PCR
SEQ ID NO: 12

What is claimed is:

1. An isolated gene comprising a DNA sequence that encodes a polypeptide having an amino acid sequence selected from the group consisting of:
   (a) SEQ ID NO: 1;
   (b) a polypeptide having 95% or more sequence homology to SEQ ID NO: 1, and having at least the ability to reduce 2,2,2-trifluoroacetophenone to 2,2,2-trifluoro-1-phenylethanol;
   (c) a polypeptide encoded by DNA of SEQ ID NO: 2;
   (d) a polypeptide encoded by DNA having 95% or more homology to SEQ ID NO: 2, and having at least the ability to reduce 2,2,2-trifluoroacetophenone to 2,2,2-trifluoro-1-phenylethanol;
   (e) a polypeptide encoded by DNA that hybridizes under stringent conditions with the complementary sequence to SEQ ID NO: 2, the stringent conditions comprising conducting the hybridization in a solution containing 50% formamide under a high ion concentration of 6×SSC at 65° C., and then washing under a low ion concentration of 0.1×SSC at 65° C. wherein the polypeptide has at least the ability to reduce 2,2,2-trifluoroacetophenone to 2,2,2-trifluoro-1-phenylethanol;
   (f) a polypeptide having 90% or more sequence homology with SEQ ID NO:1, wherein the polypeptide has at least the ability to reduce 2,2,2-trifluoroacetophenone to 2,2,2-trifluoro-1-phenylethanol and wherein the polypeptide is obtained from a microorganism belonging to the genus *Leifsonia*; and
   (g) a polypeptide having 90% or more sequince homology with SEQ ID NO: 1, wherein the polypeptide has at least the ability to reduce 2,2,2-trifluoroacetophenone to 2,2,2-trifluoro-1-phenylethanol and wherein the polypeptide is obtained from *Leifsonia* sp. S-749.

2. The isolated gene according to claim 1 further comprising a linked promoter.

3. A recombinant vector comprising the gene according to claim 1.

4. A transformant obtained by introducing into an isolated host cell the gene according to claim 2 or a recombinant vector that comprises a gene comprising a DNA encoding a polypeptide selected from the group consisting of:
   (a) SEQ ID NO:1;
   (b) a polypeptide having 95% or more sequence homology with SEQ ID NO: 1, wherein the polypeptide has at least the ability to reduce 2,2,2-trifluoroacetophenone to 2,2,2-trifluoro-1-phenylethanol;
   (c) a polypeptide encoded by DNA of SEQ ID NO: 2;
   (d) a polypeptide encoded by DNA having 95% or more sequence homology with SEQ ID NO: 2, wherein the polypeptide has at least the ability to reduce 2,2,2-trifluoroacetophenone to 2,2,2-trifluoro-1-phenylethanol;
   (e) a polypeptide encoded by DNA that hybridizes under stringent conditions with the complementary nucleotide sequence of SEQ ID NO: 2, the stringent conditions comprising conducting the hybridization in a solution containing 50% formamide under a high ion concentration of 6×SSC at 65° C., and then washing under a low ion concentration of 0.1×SSC at 65° C., wherein the amino acid sequence has at least the ability to reduce 2,2,2-trifluoroacetophenone to 2,2,2-trifluoro-1-phenylethanol;

(f) a polypeptide having a sequence homology of 90% or more with SEQ ID NO: 1, wherein the polypeptide is obtained from a microorganism belonging to the genus *Leifsonia*, and has at least the ability to reduce 2,2,2-trifluoroacetophenone to 2,2;2-trifluoro-1-phenylethanol; and (g) a polypeptide having a sequence homology of 90% or more with SEQ ID NO: 1, wherein the polypeptide has at least the ability to reduce 2,2,2-trifluoroacetophenone to 2,2,2-trifluoro-1-phenylethanol and wherein the polypeptide is obtained from *Leifsonia* sp. S-749.

5. The transformant according to claim 4, wherein the host cell is a microorganism.

6. The transformant according to claim 4, wherein the host cell is *E. coli*.

7. A transformant obtained by introducing the gene according to claim 1 into an isolated host cell.

8. A method for producing a transformant, wherein the method comprises introducing the recombinant vector according to claim 3 into a host cell.

* * * * *